United States Patent
Shelton, IV et al.

(10) Patent No.: US 10,231,775 B2
(45) Date of Patent: Mar. 19, 2019

(54) ROBOTIC SURGICAL SYSTEM WITH TOOL LIFT CONTROL

(71) Applicant: Ethicon Endo-Surgery, LLC, Guaynabo, PR (US)

(72) Inventors: Frederick E. Shelton, IV, Hillsboro, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 385 days.

(21) Appl. No.: 15/237,691

(22) Filed: Aug. 16, 2016

(65) Prior Publication Data

US 2018/0049798 A1    Feb. 22, 2018

(51) Int. Cl.
*A61B 34/30* (2016.01)
*A61B 18/14* (2006.01)
(Continued)

(52) U.S. Cl.
CPC .. *A61B 18/1442* (2013.01); *A61B 17/320068* (2013.01); *A61B 34/30* (2016.02); *A61B 34/37* (2016.02); *A61B 2017/00026* (2013.01)

(58) Field of Classification Search
CPC .... A61B 17/320092; A61B 17/320068; A61B 18/1442; A61B 18/1445; A61B 2017/320072; A61B 2017/00017; A61B 2017/00022; A61B 2017/320094; A61B 2018/00875; A61B 2018/00839; A61B 34/30
See application file for complete search history.

(56) References Cited

U.S. PATENT DOCUMENTS 8,114,345 B2    2/2012  Dlugos, Jr. et al.
8,882,792 B2    11/2014 Dietz et al.
(Continued)

FOREIGN PATENT DOCUMENTS

EP    1839599 A1    10/2007

OTHER PUBLICATIONS

International Search Report and Written Opinion for PCT/US2017/046449 dated Nov. 21, 2017 (11 pages).
(Continued)

*Primary Examiner* — Michael Peffley
(74) *Attorney, Agent, or Firm* — Mintz Levin Cohn Ferris Glovsky and Popeo, P.C.

(57) ABSTRACT

A robotic surgical system is provided that includes an electromechanical tool coupled to a surgical instrument such as an end effector adapted to apply ultrasound energy to tissue when the end effector holds the tissue. The electromechanical tool is mounted on an electromechanical arm and configured to move relative to the arm. A controller operatively coupled to the tool and the arm measures electrical impedance of tissue as ultrasound energy is applied to the tissue by the end effector. The controller determines, based on the tissue impedance measurements, that the tissue is fully cauterized. In response to the detection, the surgical system automatically lifts the end effector, either by lifting the arm to which it is coupled or independently from that arm, thereby the end effector cuts the cauterized tissue to complete the tissue cauterization/cutting. The controller also determines and controls a velocity with which the end effector is lifted.

21 Claims, 14 Drawing Sheets

(51) Int. Cl.
  *A61B 17/32* (2006.01)
  *A61B 34/37* (2016.01)
  *A61B 17/00* (2006.01)

(56) References Cited

U.S. PATENT DOCUMENTS

| | | |
|---|---|---|
| 8,915,842 B2 | 12/2014 | Weisenburgh, II et al. |
| 8,931,682 B2 | 1/2015 | Timm et al. |
| 8,945,098 B2 | 2/2015 | Seibold et al. |
| 9,351,754 B2* | 5/2016 | Vakharia ........ A61B 17/320092 |
| 2008/0081948 A1 | 4/2008 | Weisenburgh et al. |
| 2009/0254080 A1 | 10/2009 | Honda |
| 2011/0118709 A1 | 5/2011 | Burbank |
| 2011/0118778 A1 | 5/2011 | Burbank |
| 2013/0282052 A1 | 10/2013 | Aranyi et al. |
| 2014/0005718 A1 | 1/2014 | Shelton, IV et al. |
| 2016/0375272 A1* | 12/2016 | Tsubuku ........ A61B 17/320068 601/2 |

OTHER PUBLICATIONS

Correlated Solutions, "Principle of Digital Image Correlation," 2013 (http://correlatedsolutions.com/digital-image-correlation/).
U.S. Appl. No. 15/131,963 entitled "Method for Operating a Surgical Instrument" filed Apr. 18, 2016.
U.S. Appl. No. 15/177,430 entitled "Surgical Instrument With User Adaptable Techniques" filed Jun. 9, 2016.

* cited by examiner

ROBOTIC SURGICAL SYSTEM WITH TOOL LIFT CONTROL

FIELD

Methods and devices are provided for robotic surgery, and, in particular, for automating aspects of procedures performed when using a robotic surgical system.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

A robotic surgical system and corresponding methods are provided for cutting and cauterizing tissue.

In some aspects, a surgical system is provided that in some implementations includes an electromechanical arm configured for movement in multiple axes, an electromechanical tool having an instrument shaft and an end effector formed thereon, the electromechanical tool being configured to be mounted on the electromechanical arm, and a controller operatively coupled to the electromechanical arm and the electromechanical tool. The electromechanical tool is configured to move relative to the electromechanical arm and apply ultrasonic energy to tissue held by the end effector. The controller is configured to receive, during an application of ultrasonic energy to the tissue, a plurality of measurements of an electrical impedance of the tissue. The controller is further configured to detect, based on the received plurality of measurements, an increase in electrical impedance of the tissue, following a period of decreasing electrical impedance of the tissue, and, in response to detecting the increase in electrical impedance of the tissue, cause a lift of the electromechanical tool.

The surgical system can vary in any number of ways. For example, the controller can cause the lift of the electromechanical tool independently of the electromechanical arm. As another example, the controller can cause the lift of the electromechanical tool by causing a lift of the electromechanical arm.

In some embodiments, the controller causes the lift of the electromechanical tool at a lift velocity determined at least in part based on the received plurality of measurements. Detecting the increase in electrical impedance of the tissue by the controller includes detecting that the electrical impedance of the tissue has reached a threshold value. The controller can be further configured to determine an amount of time required for the electrical impedance of the tissue to reach the threshold value, determine, based at least in part on the amount of time, a lift velocity, and cause the lift of the electromechanical tool at the determined lift velocity.

The amount of time required for the electrical impedance of the tissue to reach the threshold value corresponds to at least one characteristic of the tissue. The at least one characteristic of the tissue can include a type, size and/or thickness of the tissue.

In some embodiments, the lift velocity has a first value when the tissue is small and/or thin, and the lift velocity has a second value that is smaller than the first value when the tissue is large and/or thick.

The end effector includes sensor circuitry adapted to measure the electrical impedance of the tissue while the end effector is applying ultrasonic energy to the tissue.

In some aspects, a method of operating a surgical instrument is provided that in some implementations includes applying ultrasonic energy to a tissue using a surgical instrument formed on an instrument shaft of an electromechanical tool, the electromechanical tool being configured to be mounted on an electromechanical arm. The method further includes receiving, during an application of ultrasonic energy to the tissue, a plurality of measurements of an electrical impedance of the tissue, and detecting, based on the received plurality of measurements, an increase in electrical impedance of the tissue, following a period of decreasing electrical impedance of the tissue, and, in response to detecting the increase in electrical impedance of the tissue, causing a lift of the electromechanical tool.

The method can vary in any number of ways. For example, the method can further include causing the lift of the electromechanical tool independently of the electromechanical arm. As another example, the method can further include causing the lift of the electromechanical tool by causing a lift of the electromechanical arm. The lift of the electromechanical tool causes the tissue to be cut by placing tension across the tissue.

In some embodiments, detecting the increase in electrical impedance of the tissue by the controller includes detecting that the electrical impedance of the tissue has reached a threshold value. The method can include determining that the tissue is fully cauterized when it is detected the electrical impedance of the tissue has reached the threshold value. In some embodiments, the method can include determining an amount of time required for the electrical impedance of the tissue to reach the threshold value, determining, based at least in part on the amount of time, a lift velocity, and causing the lift of the electromechanical tool at the determined lift velocity.

The amount of time required for the electrical impedance of the tissue to reach the threshold value corresponds to at least one characteristic of the tissue. The at least one characteristic of the tissue includes a type, size and/or thickness of the tissue.

In some embodiments, the method further includes detecting, based at least in part on the plurality of electrical impedance measurements, following the period of decreasing electrical impedance of the tissue and prior to detecting the increase in electrical impedance of the tissue, that the electrical impedance of the tissue has plateaued and/or reached an inflection point.

In some aspects, a method of operating a surgical instrument is provided that in some implementations includes applying ultrasonic energy to a tissue using a surgical instrument formed on an instrument shaft of an electromechanical tool, the electromechanical tool being configured to be mounted on the electromechanical arm, receiving, during an application of ultrasonic energy to the tissue, a plurality of measurements of an electrical impedance of the tissue, detecting, based on the received plurality of measurements, a target trajectory of the electrical impedance of the tissue, and, in response to detecting the target trajectory, causing a lift of the electromechanical tool.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

BRIEF DESCRIPTION OF THE DRAWINGS

The present disclosure will be more fully understood from the following detailed description taken in conjunction with the accompanying drawings, in which.

Figure 1:
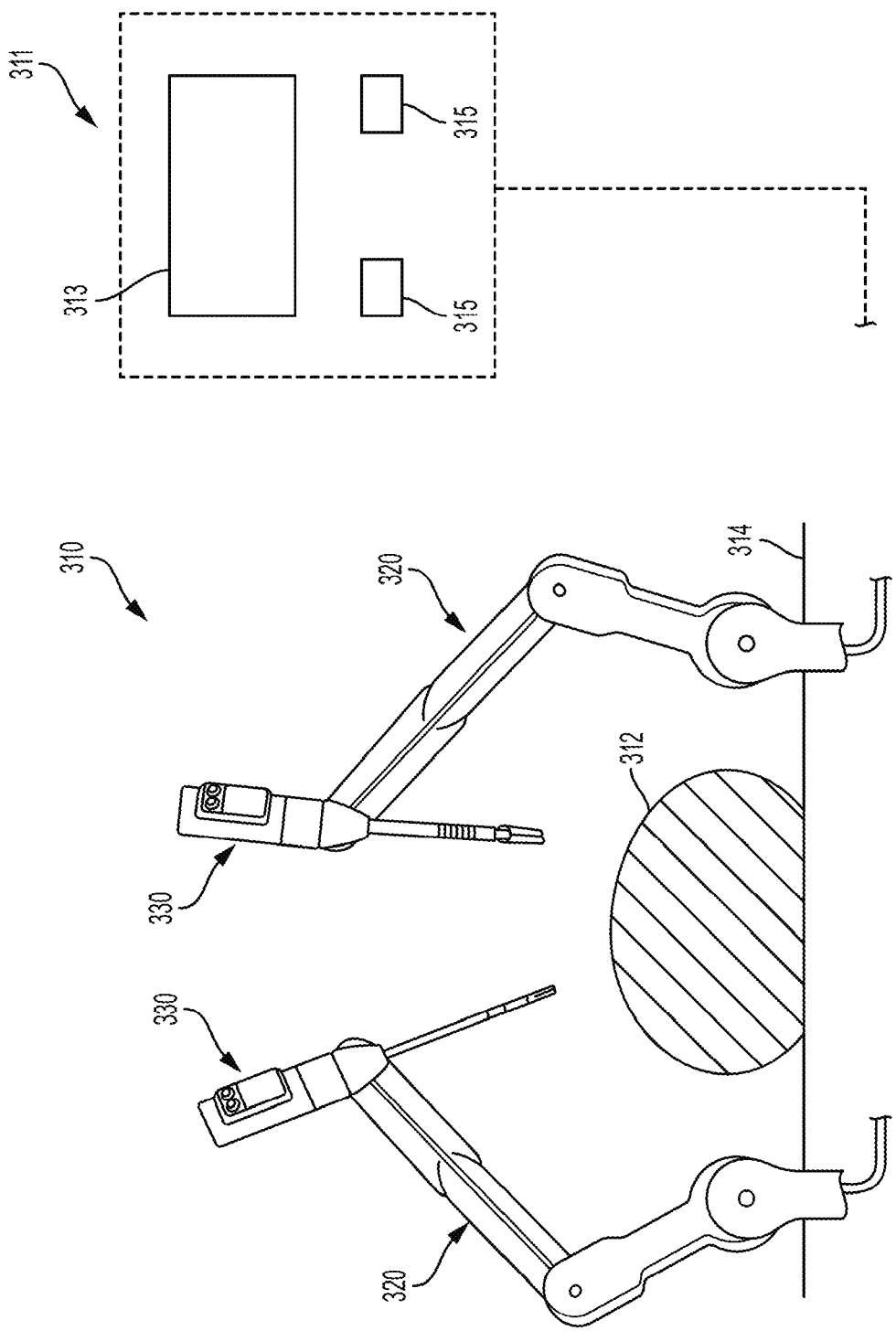
FIG. 1 illustrates a perspective view of an embodiment of a surgical robotic system.

Like labels are used to refer to same or similar items in the drawings.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, ultrasonic energy can be used to cut and cauterize (or coagulate) tissue during surgical procedures. Certain surgical instruments can be adapted to apply ultrasonic energy to tissue, which acts to cut tissue while at the same time creating a seal in the tissue by denaturing the proteins (e.g., collagen). Such ultrasonic energy-applying instruments are typically lifted by a surgeon, based on feel and experience, at the end of a cutting/sealing procedure, while still grasping tissue, to create tension on the tissue and to complete the seal. The timing of the lifting maneuver is critical and should only be attempted when the tissue is sufficiently cauterized, i.e., the energy density applied to the tissue is sufficient. Other variables that influence the effectiveness of a seal include the clamping pressure applied to tissue by grasping jaws, and the lift velocity. According to implementations of a robotic surgical system described herein, the robotic system can determine the appropriate timing for lifting a cutting/sealing instrument based on measurements of electrical impedance of the tissue, which can indicate when the tissue is fully cauterized. In addition to automating the timing of the lifting procedure, the robotic system can also determine the appropriate clamping pressure and velocity of the lift based on other variables, including tissue type and thickness as well as other tissue characteristics, such as impedance.

Robotic Surgical Systems

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Robotic System

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
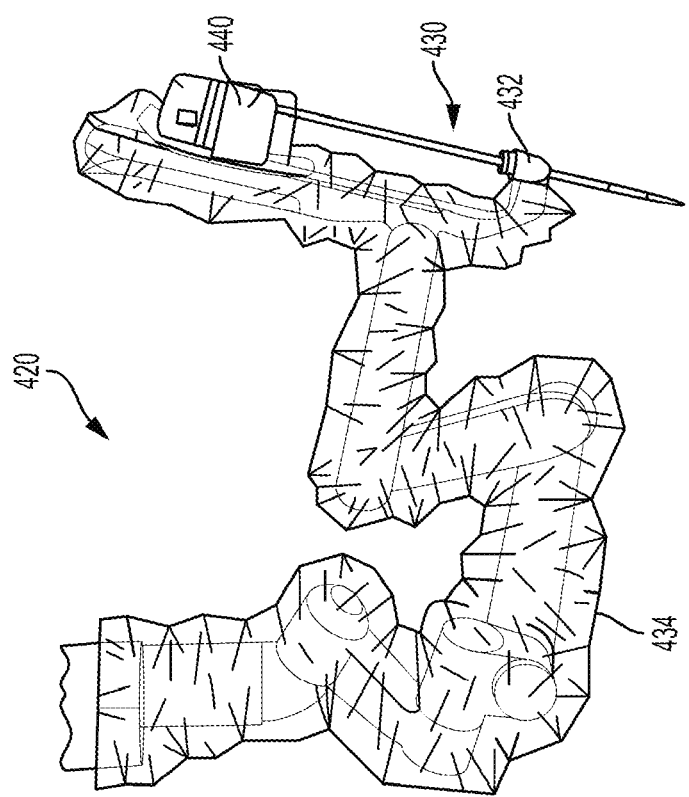
FIG. 2 illustrates an embodiment of a robotic arm and a tool assembly releasably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
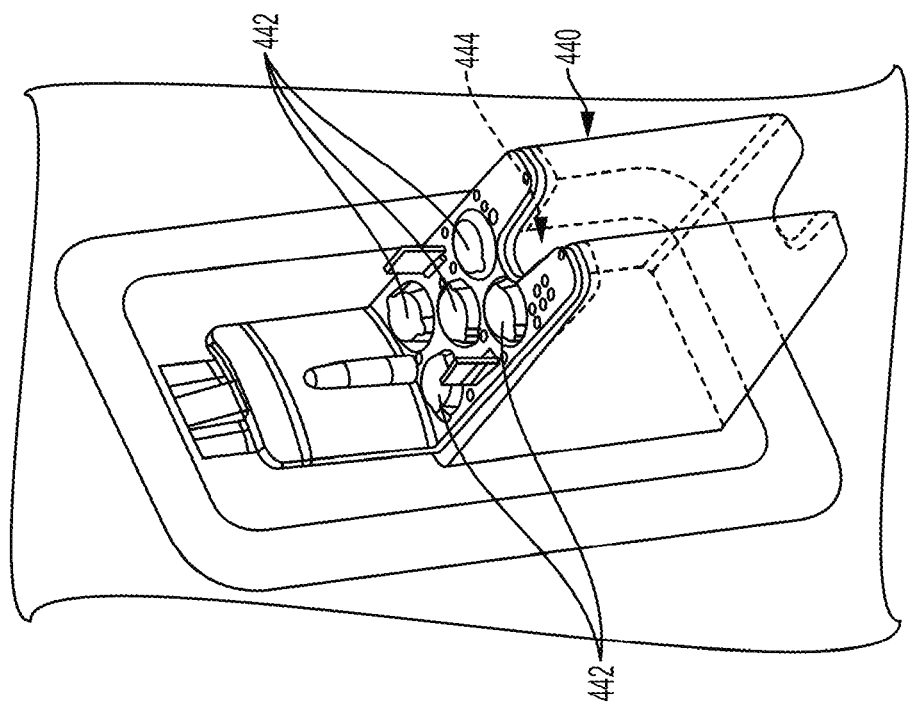
FIG. 3 illustrates an embodiment of a tool driver.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
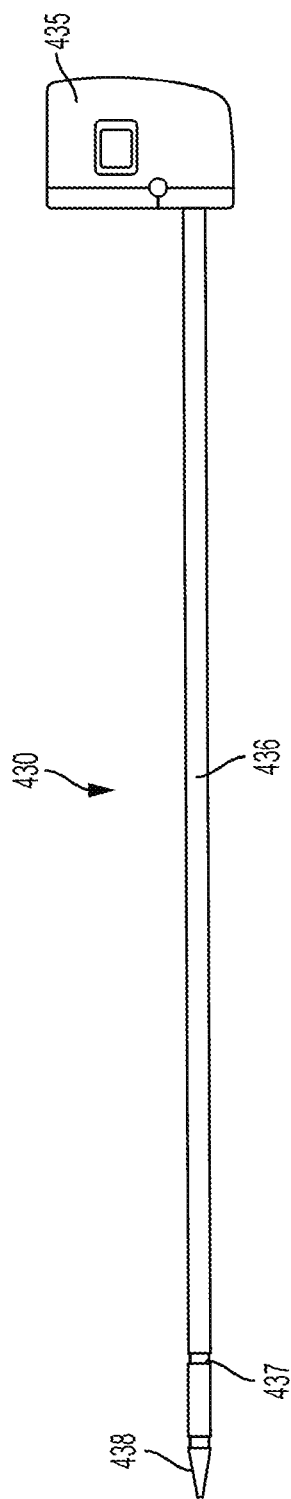
FIG. 4 illustrates an embodiment of a tool assembly uncoupled from a robotic arm.

FIG. 4 illustrates the tool assembly 430 uncoupled from the robotic arm 420. The tool assembly 430 includes a housing or puck 435 coupled to a proximal end of a shaft 436 and an end effector 438 coupled to a distal end of the shaft 436. The puck 435 can include coupling features that assist with releasably coupling the puck 435 to the tool driver 440 of the robotic arm 420. The puck 435 can include gears and/or actuators that can be actuated by the one or more motors 442 in the driver 440, as will be described in greater detail below. The gears and/or actuators in the puck 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the puck 435, or it can be releasably coupled to the puck 435 such that the shaft 436 can be interchangeable with other shafts. This can allow a single puck 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 5:
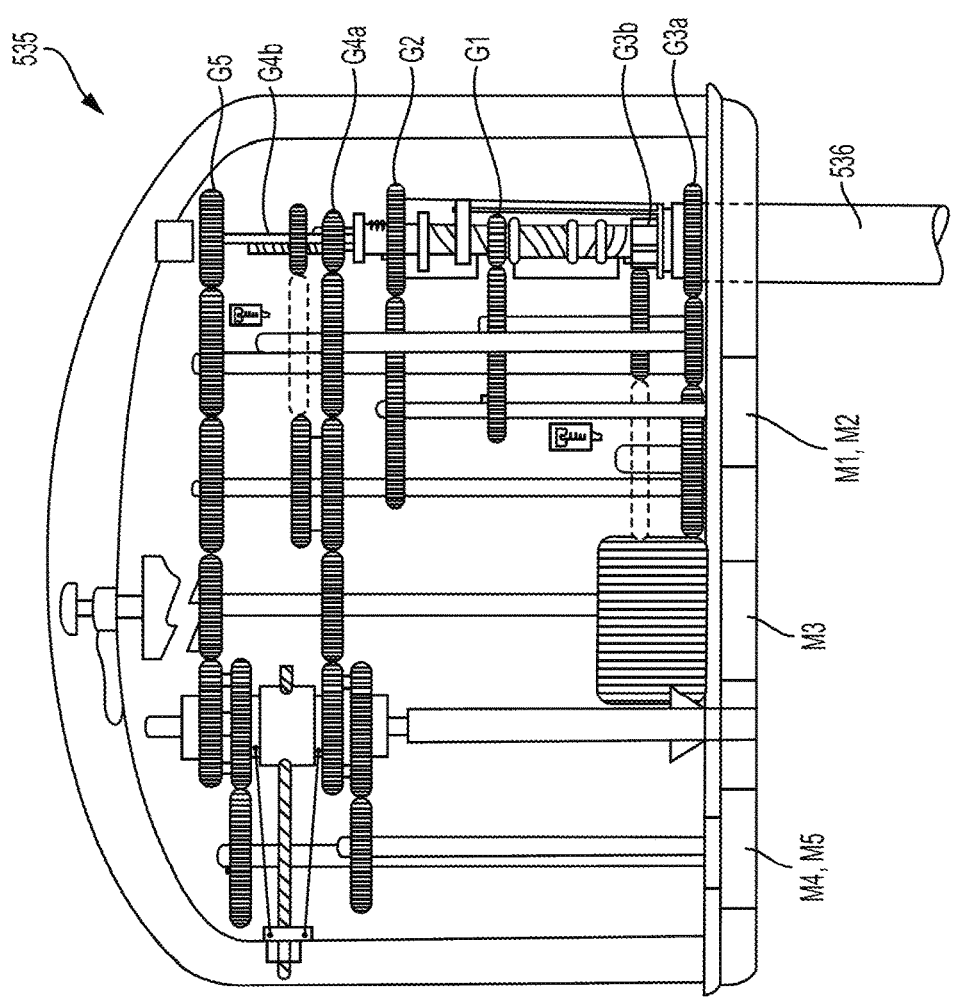
FIG. 5 illustrates an embodiment of a puck and a proximal end of a shaft extending from the puck.

FIG. 5 illustrates an embodiment of a puck 735 and a proximal end of a shaft 736 extending from the puck 735. As shown in FIG. 5, the puck 735 includes a plurality of actuation gears and gear shafts that can be either directly or indirectly controlled by any one of the motors 442 associated with the driver 440. For example, as shown in FIG. 5, the puck 735 is configured to couple to five motors at the locations indicated by reference numbers M1, M2, M3, M4, and M5. In this embodiment, puck 735 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of the end effector 438 in desired left and right directions. The puck 735 also includes a shaft rotation gear G3a that is coupled to the third motor M3 via a series of one or more additional gears and shafts. Actuation of the third motor M3 will thus rotate the shaft rotation gear G3a thereby causing rotation of the shaft 436 of the tool assembly 430. The third motor M3 can also be configured to shift and to couple, via a series of one or more additional gears and shafts, to a head rotation gear G3b, which will cause rotation of the end effector 438 relative to the shaft 436. The puck 735 further includes a firm close gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector 438. The puck 735 further includes a quick close gear G4b that can also couple to the fourth motor M4 via a series of one or more additional gears and shafts. When motor M4 is shifted into engagement with the quick close gear G4b, actuation of the fourth motor M4 will rotate the quick close gear G4b to cause linear translation of a quick close cable to quickly close the jaws of the end effector 438. Finally, the illustrated puck 735 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector 438, as will be discussed in more detail below.

Figure 6:
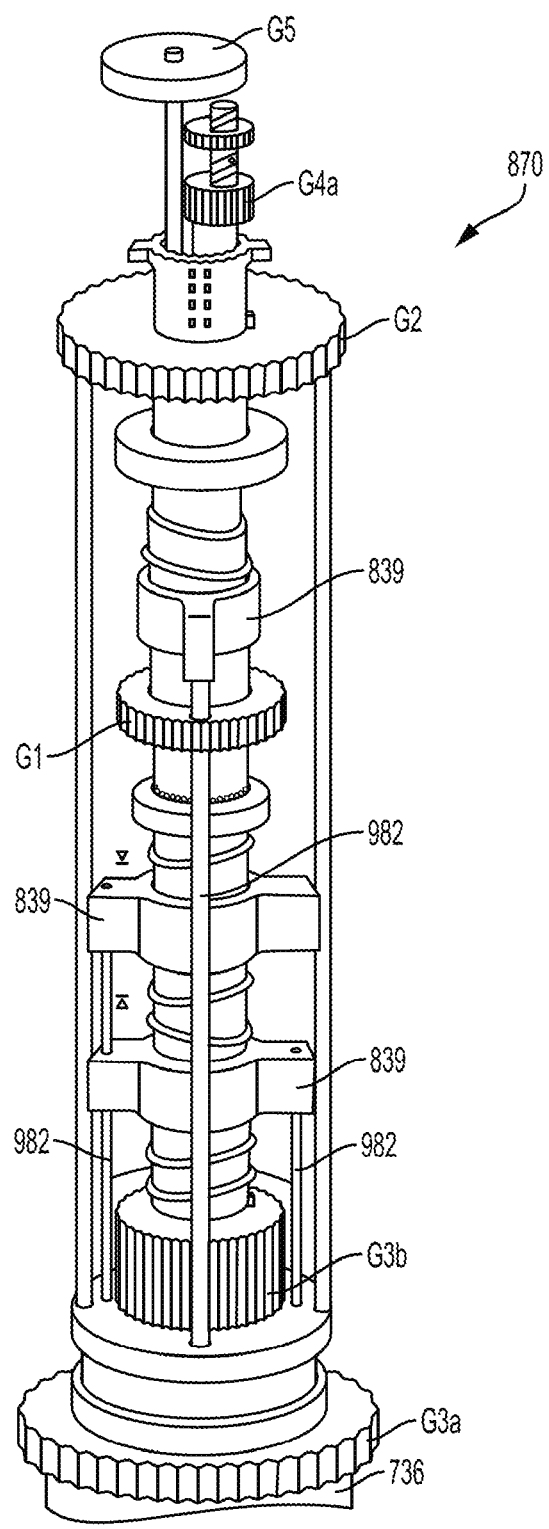
FIG. 6 illustrates an embodiment of the actuation assembly components of a puck.
Figure 7:
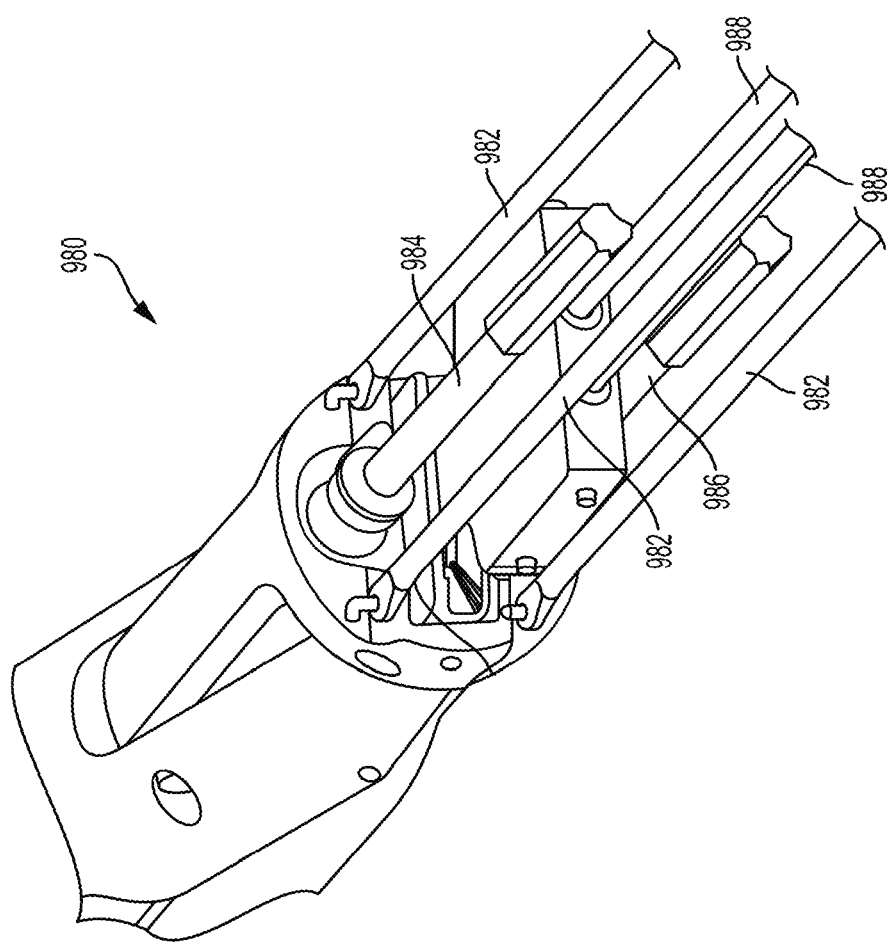
FIG. 7 illustrates a distal end of actuation shafts extending from a wrist located just proximal of an end effector.

FIG. 6 illustrates the actuation assembly 870 components of the puck of FIG. 5. As shown and indicated above, each of the gears G1-G5 is coupled to an actuation shaft that extends from the actuation assembly 870 and along the shaft 436 of the tool assembly 430, such as for controlling the movements of the end effector. FIG. 7 illustrates a distal end of the actuation shafts extending from a wrist 980 located just proximal of the end effector 438. The wrist 980 can allow for fine movements and angulation of the end effector 438 relative to the proximal end of the shaft 436. As shown in FIG. 7, the wrist 980 includes four articulation cables 982 that are spaced around a perimeter of the wrist 980. When actuated pushed, pulled, rotated), the articulation cables 982 will cause articulation of the end effector 438 (e.g., movement up, down, left, right, and combinations thereof) relative to the proximal end of the shaft 436. The articulation cables 982 are connected to the articulation couplers 839, shown in FIG. 6, that are driven proximally and distally when the articulation gears G1, G2 are actuated by the first and second motors M1, M2. The wrist 980 also includes an upper rotary driver 984 that when actuated can cause the pair of jaws of the end effector 438 to firmly close. The upper rotary driver 984 is coupled to the firm close gear G4a shown in FIG. 6 such that rotation of the firm close gear G4a by the motor M4 causes rotation of the rotary driver 984. The wrist 980 can also include a lower rotary driver 986 that when actuated can cause movement of a sled located at the end effector 438. The lower rotary driver 986 is coupled to the firing gear G5 shown in FIG. 6 and it likewise rotates in response to rotation of the firing gear G5. The illustrated wrist 980 further includes a linear pull cable 988 that is coupled to the quick close gear G4b shown in FIG. 6 and that moves linearly in a proximal direction to cause rapid close of the pair of jaws.

Figure 8:
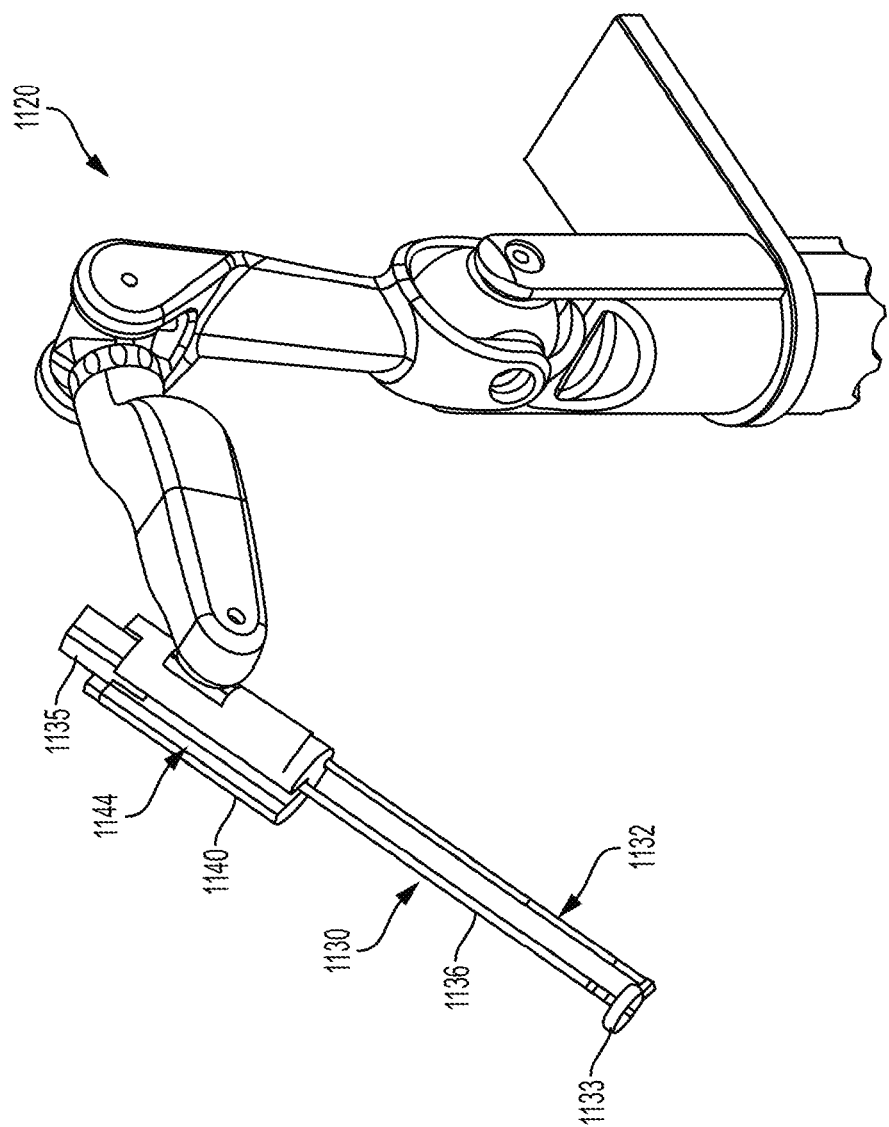
FIG. 8 illustrates an embodiment of a robotic arm and a tool assembly releasably coupled to the robotic arm.

FIG. 8 illustrates another embodiment of a robotic arm 1120 and a tool assembly 1130 releasably coupled to the robotic arm 1120. The robotic arm 1120 can support and move the associated tool assembly 1130 along one or more mechanical degrees of freedom (e.g., all six Cartesian degrees of freedom, five or fewer Cartesian degrees of freedom, etc.).

The robotic arm 1120 can include a tool driver 1140 at a distal end of the robotic arm 1120, which can assist with controlling features associated with the tool assembly 1130. The robotic arm 1120 can also include a movable tool guide 1132 that can retract and extend relative to the driver 1140. A shaft of the tool assembly 1130 can extend parallel to a threaded shaft of the movable tool guide 1132 and can extend through a distal end feature 1133 (e.g., a ring) of the movable tool guide 1130 and into a patient.

In order to provide a sterile operation area while using the surgical system, a barrier (not shown) can be placed between the actuating portion of the surgical system (e.g., the robotic arm 1120) and the surgical instruments (e.g., the tool assembly 1130) in the sterile surgical field. A sterile component, such as an instrument sterile adapter (ISA), can also be placed at the connecting interface between the tool assembly 1130 and the robotic arm 1120. The placement of an ISA between the tool assembly 1130 and the robotic arm 1120 can ensure a sterile coupling point for the tool assembly 1130 and the robotic arm 1120. This permits removal of tool assemblies 1130 from the robotic arm 1120 to exchange with other tool assemblies 1130 during the course of a surgery without compromising the sterile surgical field.

Figure 9:
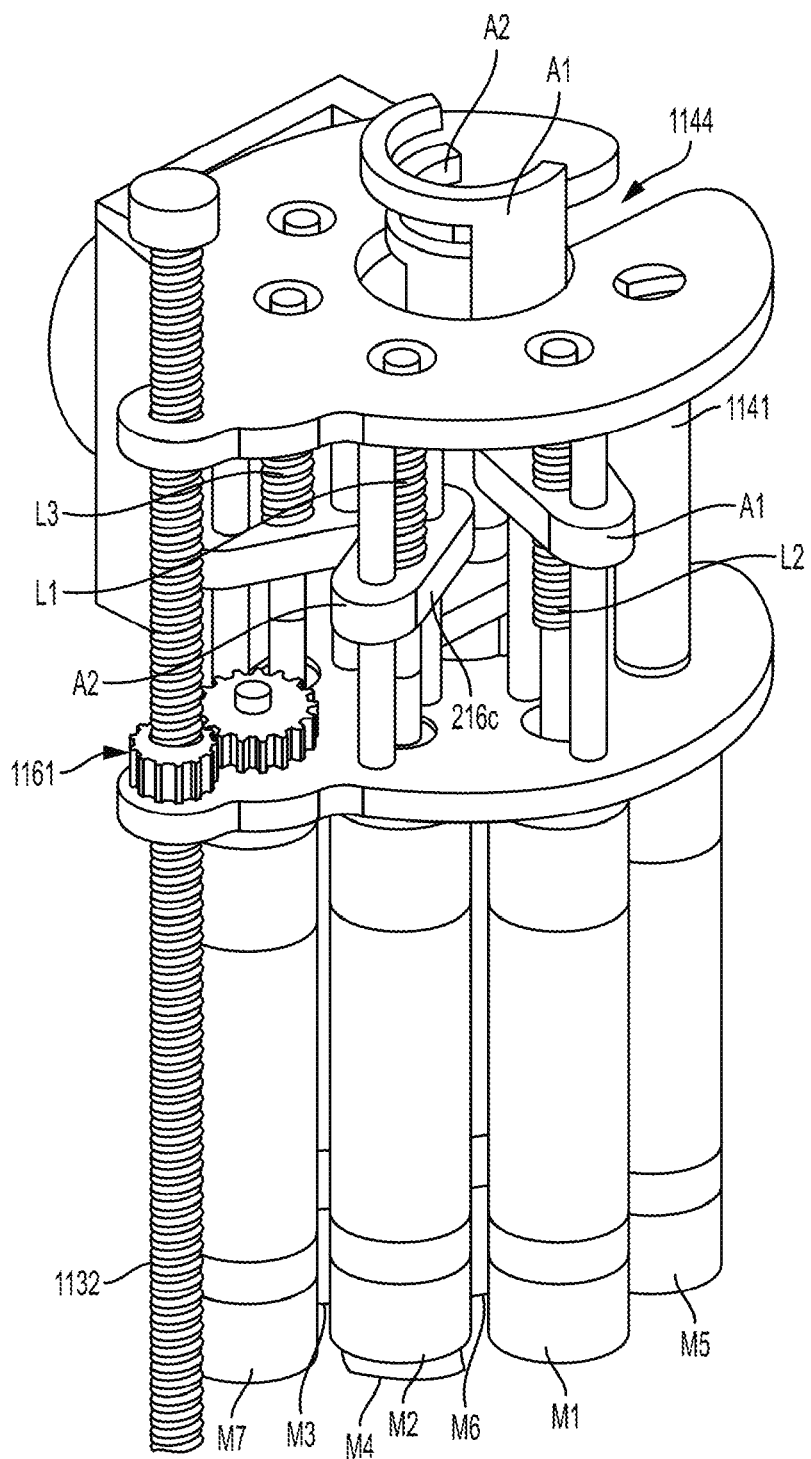
FIG. 9 illustrates an embodiment of a tool driver.

FIG. 9 illustrates the tool driver 1140 in more detail. As shown, the tool driver 1140 includes one or more motors, e.g., seven motors M1-M7 are shown, that control a variety of movements and actions associated with the tool assembly 1130, as will be described in greater detail below. The driver 1140 can also include one or more lead screws (e.g., three lead screws L1, L2, and L3 are shown) that can be individually rotated by a motor and, as a result of the rotation of the lead screw, cause linear and/or rotational movement of at least one actuator (e.g., see, for example, actuators A1 and A2 shown in FIG. 9). Movement of each actuator controls the movement of driving members (e.g., gears, cables) located in the tool assembly 1130 for controlling one or more actions and movements that can be performed by the tooling assembly 1130, such as for assisting with performing a surgical operation. The actuators extend from a top end of the driver 1140 for coupling to the driving members of the tool assembly 1130 mounted on top of the tool driver 1140.

The tool assembly 1130 can be loaded from a top side of the driver 1140 with the shaft of the tool assembly 1130 being positioned in a shaft-receiving channel 1144 formed along the side of the driver 1140. The shaft-receiving channel 1144 allows the shaft, which extends along a central axis of the tool assembly 1130, to extend along a central axis of the driver 1140 when the tool assembly 1130 is coupled to the driver 1140. In other embodiments, the shaft can extend through on opening in the tool driver 1140, or the two components can mate in various other configurations.

Figure 11:
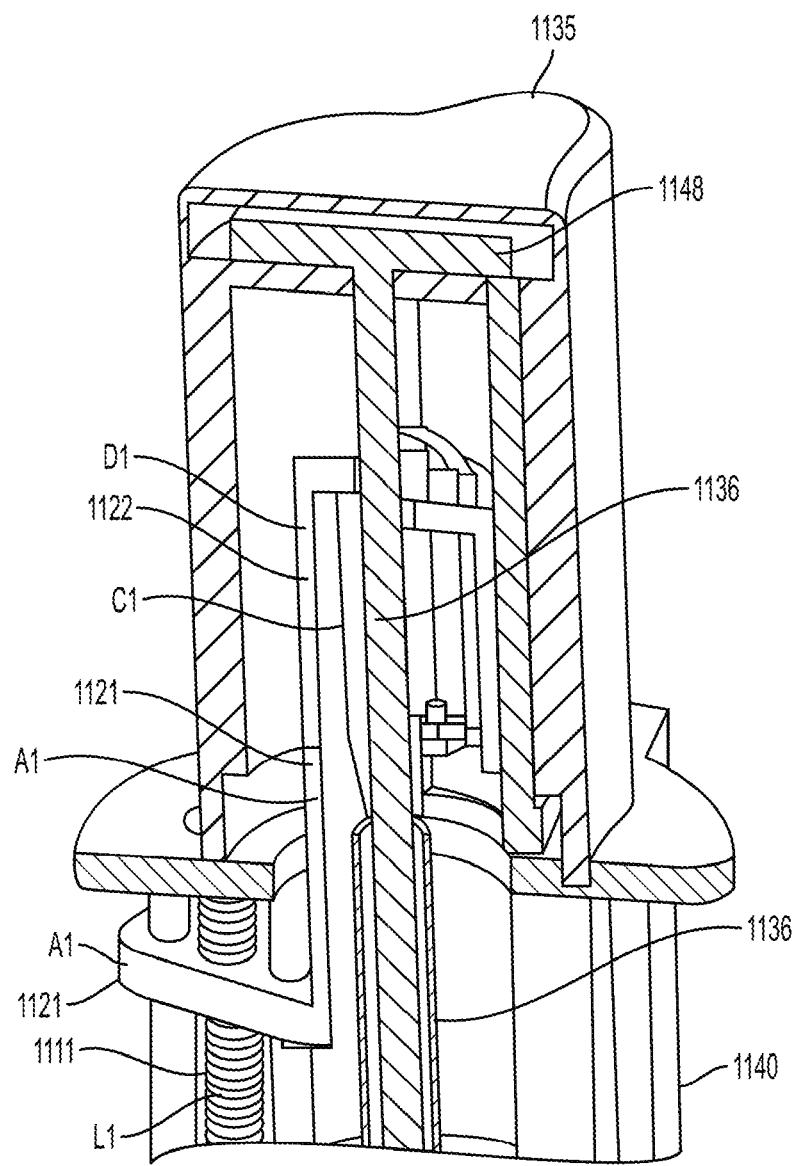
FIG. 11 illustrates an embodiment of a puck coupled to a driver with actuators extending from the driver into the puck and engaging driving member.

As shown in FIG. 11, the tool assembly 1130 includes a housing or puck 1135 coupled to a proximal end of a shaft 1136 and an end effector 1138 coupled to a distal end of the shaft 1136. The puck 1135 can include coupling features that assist with releasably coupling the puck 1135 to the tool driver 1140 of the robotic arm 1120. The puck 1135 can include driving members (e.g., gears, cables, and/or drivers) that can be directly or indirectly actuated by the one or more motors M1-M5, as will be described in greater detail below. The driving members in the puck 1135 can control the operation of various features associated with the end effector 1138 (e.g., clamping, firing, rotation, articulation, etc.), as well as control the movement of the shaft 1136 (e.g., rotation and/or articulation of the shaft).

The shaft 1136 can be releasably coupled to the puck 1135 such that the shaft 1136 can be interchangeable with other shafts. This can allow a single puck 1135 to be adaptable to various shafts 1136 having different end effectors 1138. The shaft 1136 can include actuators and connectors that extend along the shaft and assist with controlling the actuation and/or movement of the end effector 1138 and/or shaft 1136. The shaft 1136 can also include one or more joints or wrists 1137 that allow a part of the shaft 1136 or the end effector 1138 to rotate and/or articulate relative to the longitudinal axis of the shaft 1136. This can allow for fine movements and various angulation of the end effector 1138 relative to the longitudinal axis of the shaft 1136. The end effector 1138 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 10:
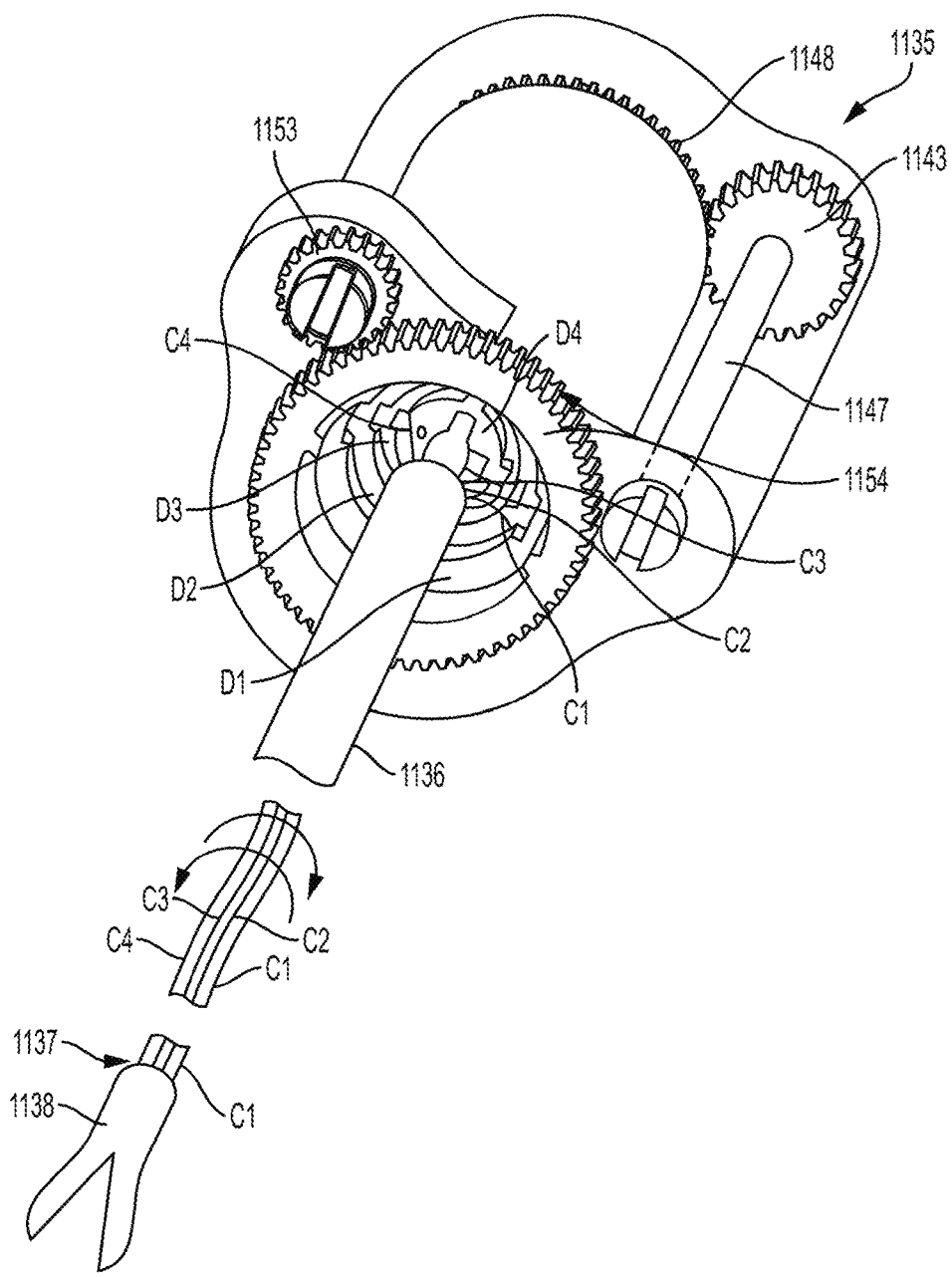
FIG. 10 illustrates a portion of a puck actuation assembly contained within a puck.

FIG. 10 illustrates a part of a puck actuation assembly contained within the puck 1135. As shown in FIG. 10, the puck 1135 includes at least one driving member (e.g., four driving members D1, D2, D3, and D4 are shown) that can each become engaged with an actuator of the driver 1140 such that actuation of an actuator causes actuation of a driving member thereby controlling the operation of various features associated with the shaft 1136 and/or end effector 1138. Each driving member D1-D4 can be coupled to a proximal end of a shaft or cable (e.g., four cables C1, C2, C3, and C4 are shown). Each cable can extend from a driving member and couple to a feature associated with either the shaft 1136 or the end effector 1138 thereby controlling a function of such feature.

FIG. 11 illustrates the puck 1135 coupled to the driver 1140 with the actuators extending from the driver 1140 into the puck 1135 and engaging the driving members. For example, motor M1 can cause lead screw L1 to rotate thereby causing actuator A1, which is threadably coupled to lead screw L1, to linearly advance in the proximal direction (towards and into the puck 1135). Actuator A1 can include an extension threadably coupled to the lead screw L1. The extension can be coupled to or integrated with a partial cylindrical shaft that extends along the longitudinal axis of the puck 1135 and the driver 1140. The partial cylindrical shaft of the actuator A1 can engage with driving member D1 such that when the actuator A1 is linearly advanced, the driving member D1 is caused to linearly advance in the same direction. Driving member D1 can be coupled to cable C1 such that when driving member D1 is advanced in the proximal direction, cable C1 is pulled in the proximal direction. Cable C1 extends along the shaft of the tool assembly 1130 and is operatively coupled to a part of the end effector 1138 thereby controlling a function of the end effector 1138 (e.g., opening and closing of jaws, deployment of a staple, etc.) when the cable is C1 translated in either the proximal or distal direction.

In some implementations, for example, four motors (e.g., M1-M4) can each individually control movement of a respective lead screw (e.g., L1-L4) thereby individually linearly translating a respective actuator (e.g., A1-A4) coupled thereto. Although the actuators are described as being linearly translated, the actuators can be linearly translated and/or rotationally moved as a result of actuation of a respective motor. Additional motors (e.g., motors M5 and M6) can be included in the driver 1140 for actuating various other aspects of the tool assembly 1130. For example, motor M5 can cause a first driver shaft 1141 to rotate, which is operatively coupled to a first puck shaft 1147 having a first puck gear 1143 coupled to a distal end of the first puck shaft 1147. Rotation of the first driver shaft 1141 thereby causes the first puck shaft 1147 and first puck gear 1143 to rotate. The first puck gear 1143 is engaged with a first shaft rotation gear 1148 that is caused to rotate as a result of the first puck gear 1143 rotating. The first shaft rotation gear 1148 is operatively coupled to the shaft 1136 of the tool assembly 1130 and can thereby cause rotation of the shaft 1136 and/or end effector 1138. Motor M6 can cause a second driver shaft to rotate, which is operatively coupled to a second puck gear 1153. The second puck gear 1153 is engaged with a second shaft rotation gear 1154 that is caused to rotate as a result of the second puck gear 1153 rotating. The second shaft rotation gear 1154 is also operatively coupled to the shaft 1136 and, upon rotation, provides additional torque through the shaft 1136 and for various features associated with the end effector 1138. Actuation of motor M7 can cause shaft gears 1161 to rotate, thereby causing the threaded shaft of the movable tool guide 1132 to linearly translate.

Terminology

Figure 12:
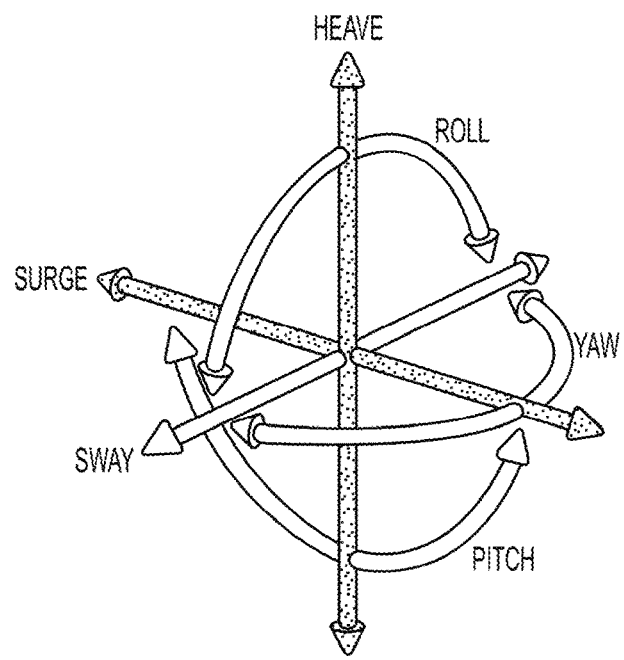
FIG. 12 illustrates the degrees of freedom of movement within a surgical robotic system.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 12, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 13:
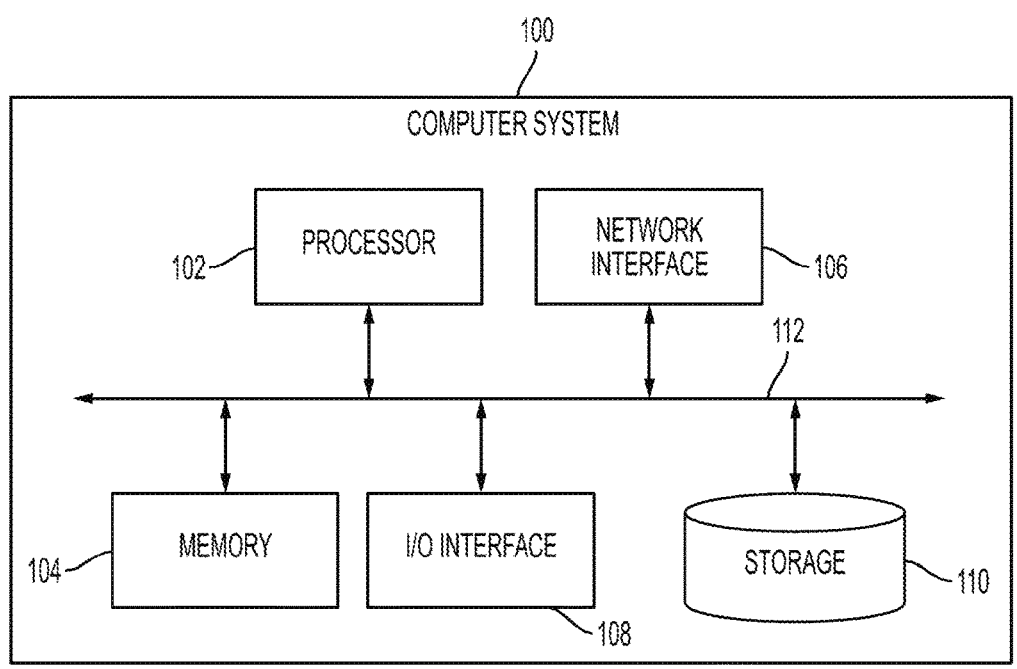
FIG. 13 illustrates an embodiment of a computer system.

FIG. 13 illustrates an embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (10) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 13 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

In some embodiments, a robotic surgical system can include an electromechanical tool assembly (e.g., tool assembly 330 in FIG. 1 or tool assembly 430 in FIGS. 2-4) including a surgical instrument adapted to apply energy, such as ultrasonic energy, to tissue held by the surgical instrument. The electromechanical tool is configured to be mounted on an electromechanical arm (e.g., robotic arm 320 in FIG. 1 or robotic arm 420 FIGS. 2 and 3) and it is configured to move relative to the electromechanical arm. The robotic surgical system further includes a controller operatively coupled to the electromechanical arm and the electromechanical tool and configured to control operation of these components.

The surgical instrument can be an end effector or other type of an instrument that can transmit ultrasonic energy through tissue to cut and cauterize and seal the tissue. After the seal in tissue is created, application of energy to the tissue is discontinued and tissue is disengaged from the end effector. As discussed above, the application of energy to tissue, and the proper cutting and sealing of tissue, is marked by a lifting maneuver. In a typical, manual surgical procedure, this is performed when the surgeon performing the procedure determines (by tactile feedback) that the tissue cauterization is complete, however since robotic surgical systems typically lack tactile feedback. The timing and duration of the lifting maneuver is essential to the success of the cutting and sealing procedure. Failure to perform this maneuver at the proper time, or for the proper amount of time, can lead to insufficient cutting or sealing, or to unintended tissue damage if too much energy is applied to the tissue.

Accordingly, the robotic surgical system described herein can automatically control a process of tissue cutting/sealing and can determine when, and with what velocity, to perform the lifting maneuver. The controller (and/or other suitable component(s) of the robotic surgical system) can be configured to receive, during an application of ultrasonic energy to the tissue, a plurality of measurements of electrical impedance of the tissue over time. After a certain target trajectory of the tissue impedance as a function of the plurality of tissue impedance measurements is observed, the surgical system can determine that the tissue is appropriately cauterized. In some embodiments, as discussed in more detail below, the controller can detect a period of decreasing electrical impedance of the tissue, which is followed by a pronounced increase in the electrical impedance of the tissue. In response to detecting such increase, the controller causes the lifting maneuver to be effected in a controlled manner, as also discussed in more detail below.

The parameters that affect the sufficiency of a tissue seal include a clamping pressure applied to tissue by instrument's grasping jaws, lift velocity, tissue characteristics (e.g., its type and thickness), impedance of the tissue, and other parameters. The end effector automatically performs the lifting maneuver at the appropriate time to properly cut and seal the tissue based on a determination by the controller that the tissue is appropriately cauterized. This determination can be done based on various parameters, such as, for example, tissue impedance, jaw's clamping pressure, and other parameters that can be measured during a surgical procedure, as the ultrasonic energy is applied to the tissue. Values of the monitored parameters can be used by the robotic surgical system to determine that the tissue is sealed as appropriate for the surgical procedure given the type of tissue, and to thus determine when and in what manner (e.g., with what lift velocity) to lift the end effector.

The robotic surgical system can be configured to lift the end effector in any suitable way. For example, the surgical system can lift the electromechanical tool having the end effector coupled thereto, independently of a robotic arm to which the tool is coupled. In some embodiments, however, the surgical system can lift the electromechanical tool with the end effector by lifting the robotic arm. Regardless of the specific way in which the end effector is lifted, the surgical procedure as described herein may not be dependent on a surgeon's subjective and therefore potentially error-prone determination when and in which way to disassociate the end effector from the tissue.

Figure 14A:
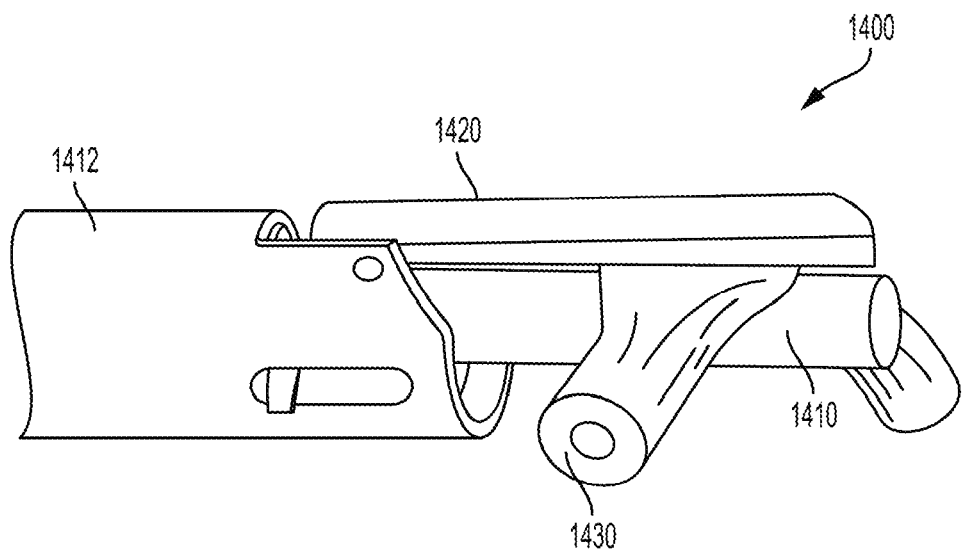
FIG. 14A illustrates an embodiment of an end effector configured to apply ultrasound energy to tissue.
Figure 14B:
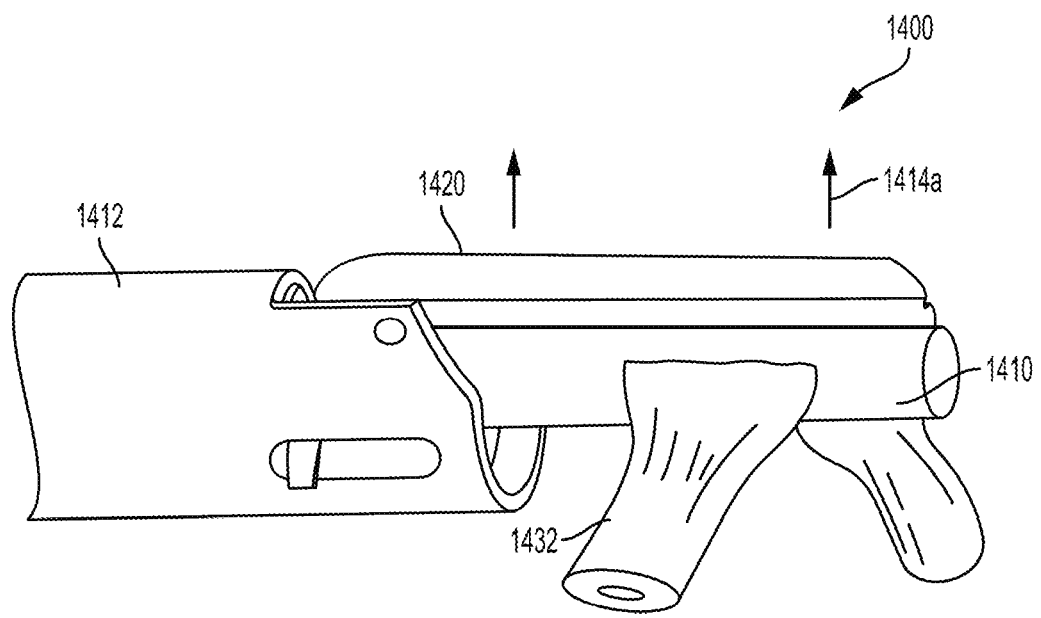
FIG. 14B illustrates a lift of the end effector of FIG. 14A.

FIGS. 14A and 14B illustrate an embodiment of an end effector 1400 of a robotic surgical system in accordance with the described techniques. Other components of the surgical system are not shown in FIGS. 14A and 14B for the sake of simplicity. The end effector 1400 is adapted to cut and seal tissue by applying ultrasonic or other type of energy thereto. The end effector 1400 can be positioned at a distal end 1412 of an instrument shaft of an electromechanical tool assembly (not shown), such as, for example, the tool assembly 330 (FIG. 1) or 430 (FIGS. 2-4). The tool assembly can be releasably mounted on an electromechanical robotic arm such as, for example, the robotic arm 320 (FIG. 1) or 420 (FIGS. 2 and 3). The end effector can be, for example, the end effector 438 (FIG. 4), or any other type of a surgical instrument configured to apply ultrasonic energy or other form of energy to tissue to cut and coagulate it. The tool assembly is configured to move relative to the electromechanical arm.

As shown in FIG. 14A, the end effector 1400 includes a lower jaw or ultrasonic blade 1410, and an upper jaw or clamp member 1420 that are configured to clamp tissue therebetween. In this example, the end effector 1400 is shown in operation, when tissue 1430 is clamped between the blade and clamp member 1410, 1420. In the illustrated example, the tissue 1430 is in the form of a blood vessel. A person skilled in the art will appreciate, however, that the tissue can be any other type of tissue.

The blade and clamp member 1410, 1420 can have a variety of different configurations. The clamp member 1410 has a tissue-facing surface shaped and sized such that tissue can be grasped between the clamp member 1410 and the blade 1420. The tissue-facing surface can have various surface features that facilitate grasping and retaining of tissue between the jaws of the end effector 1400. The features formed on the tissue-facing surface can form various patterns, including a combination of patterns.

The blade 1420 can be shaped in a suitable manner so as to cut tissue when vibrations at ultrasound frequencies are applied thereto. The end effector 1400 can include a transmission element or waveguide (not shown separately) that is adapted to transmit ultrasonic energy from a suitable energy source to the blade 1410. The blade 1410 can be integral with the waveguide so as to form a single unit, or they can be separate elements connected to one another in a suitable way. Regardless of the configuration of the blade and the waveguide, the blade 1410 is configured to transmit ultrasonic energy to tissue to cut and coagulate the tissue in a controlled manner.

The described robotic surgical system can include an ultrasonic transducer coupled to an ultrasonic generator via a suitable transmission medium. The ultrasonic transducer can be coupled to the waveguide to transmit ultrasound signal thereto. It should be appreciated, however, that the described robotic surgical system can have other components configured to deliver ultrasound energy to the end effector 1400. Regardless of the type, number, and configuration of such components, they can be controlled via a controller system, e.g., the control system 315 in FIG. 1, or any other controller(s).

In operation, as shown in FIG. 14A, when the clamp member 1420 is brought in proximity to the blade 1410 and the tissue 1430 is clamped therebetween, ultrasound energy is applied to the tissue 1430. FIG. 14A illustrates by way of example the end effector 1400 engaged with the tissue 1430 when cauterization of the tissue 1430 is complete. As mentioned above, the described techniques can be used to coagulate and cauterize tissue, and these processes, for the purpose of the present disclosure, are used interchangeably. Treating tissue with ultrasound energy involves destroying tissue by cauterization, which leads to coagulation of the tissue—denaturing protein in the tissue and tissue desiccation. To create an effective seal across the tissue 1430, the tissue cauterized and coagulated in a controlled manner. Thus, creation of the tissue involves a precise control over a number of parameters during cauterization, such as a power level, pressure exerted on tissues by the jaws of an end effector, lift velocity of an ultrasound blade, and other parameters.

The described surgical system automatically lifts the end effector at an appropriate velocity when it is determined that the tissue cauterization is complete. The automatic lifting can involve lifting the tool assembly (having the end effector coupled at its distal end) independently from a robotic arm to which the tool assembly is coupled or lifting both the robotic arm and the tool coupled thereto. When the end effector is lifted, tension is applied across the cauterized tissue such that the ultrasound blade (or other suitable member delivering ultrasound energy to tissue) creates a cut in the tissue, thus completing the tissue cutting/sealing.

As mentioned above, FIG. 14A illustrates the end effector 1400 when cauterization of the tissue 1430 is completed. In FIG. 14A, the blade and the clamp member 1410, 1420 are shown in contact with the tissue 1430. When the robotic surgical system determines that the cauterization of the tissue 1430 is complete, the surgical system causes the end effector 1400 to be lifted, such that the blade 1410 performs a (final) cut through the tissue. FIG. 14B illustrates that the end effector 1400 (and thus the blade 1410) is lifted, as schematically shown by arrows one of which is labeled as 1414a, and the tissue 1430 is cut, such that a portion of the tissue 1432 is disassociated from the end effector 1400 (another portion of the cut tissue 1430 is not labeled).

As mentioned above, the robotic surgical system as described herein determines when to disengage an end effector from tissue based on tissue characteristics and parameter(s) being monitored during the procedure. A target impedance trajectory as a function of measured tissue impedance can be obtained. Once it is determined that the tissue impedance has completed to follow the target impedance trajectory and that a certain impedance value is reached, the surgical system can cause the end effector to be lifted.

In some embodiments, an end effector in accordance with the described techniques (e.g., the end effector 1400 shown in FIGS. 14A and 14B or any other surgical instrument) can be adapted to measure electrical impedance of tissue to which the end effector applies ultrasound and/or other type of energy. For example, referring to the example in FIGS. 14A and 14B, the end effector 1400 can include sensor circuitry (e.g., bridge circuit or any other sensor) adapted to measure electrical impedance of the tissue 1430. A person skilled in the art will appreciate that the tissue impedance can be measured in a variety of different ways, using any suitable component(s).

During the surgical procedure, application of ultrasonic energy transmitted from the blade 1410 to the tissue 1430 can cause change in electrical impedance of the tissue 1430. As the tissue is being treated using the end effector 1400, its impedance can change such that a trajectory of the tissue impedance corresponding to these changes resembles a bathtub and can therefore be referred to as an "impedance bathtub." The tissue 1430 is considered to be fully cauterized when the changes in the electrical impedance of the tissue 1430 can be represented by a target bathtub-shaped trajectory. The "impedance bathtub" can be considered to be "complete" when the impedance value reaches a predetermined threshold value after following the target bathtub-shaped trajectory.

In the beginning of a tissue cutting/sealing procedure, when ultrasound energy is first applied to tissue, an initial value of tissue impedance can be relatively high, typically in the range of about 10-250 ohms, and more typically about 75 ohms. As the end effector continues applying ultrasonic energy to the tissue such that protein within the tissue denatures and tissue disintegrates, the tissue impedance decreases. Moreover, as the tissue is compressed between the end effector's jaws (e.g., the blade and the clamp member 1410, 1420), the electrical impedance of the tissue further decreases. The electrical impedance of the tissue can decrease until it plateaus and/or reaches an inflection point. At that point, as the fluids (e.g., water) in the tissue evaporate and the tissue is desiccated, the electrical impedance of the tissue can start to increase until a certain threshold value. The time for this sequence to occur can be about 1-10 seconds (typically about 4-6 seconds). Once that certain threshold value is reached, the tissue is considered to be fully cauterized and can be cut by lifting the end effector such that the end effector's ultrasound blade is passed through the tissue—e.g., in the manner as shown for the end effector 1400 in FIG. 14B. In this way, the end effector is automatically lifted when the electrical impedance of the tissue has followed a target trajectory, e.g., the "impedance bathtub." It should be appreciated that the target impedance trajectory can resemble other shapes, and that the "impedance bathtub" is used herein as an example of the description of the target impedance trajectory.

A person skilled in the art will appreciate that the application of energy to tissue can be terminated based solely on exceeding a final threshold impedance value, which can be in the range of about 300-500 ohms, and typically about 375-425 ohms. The are some exceptions to this, however. One exception is in the event that the timing is very short (i.e., about 1 second), in which case there is a time threshold in addition to an impedance threshold. For example, energy deliver need not terminate within a delivery period of less than 2 seconds. Further, energy delivery can be effected for a period of at least 2 seconds with an impedance value above 400 ohms.

Figure 15:
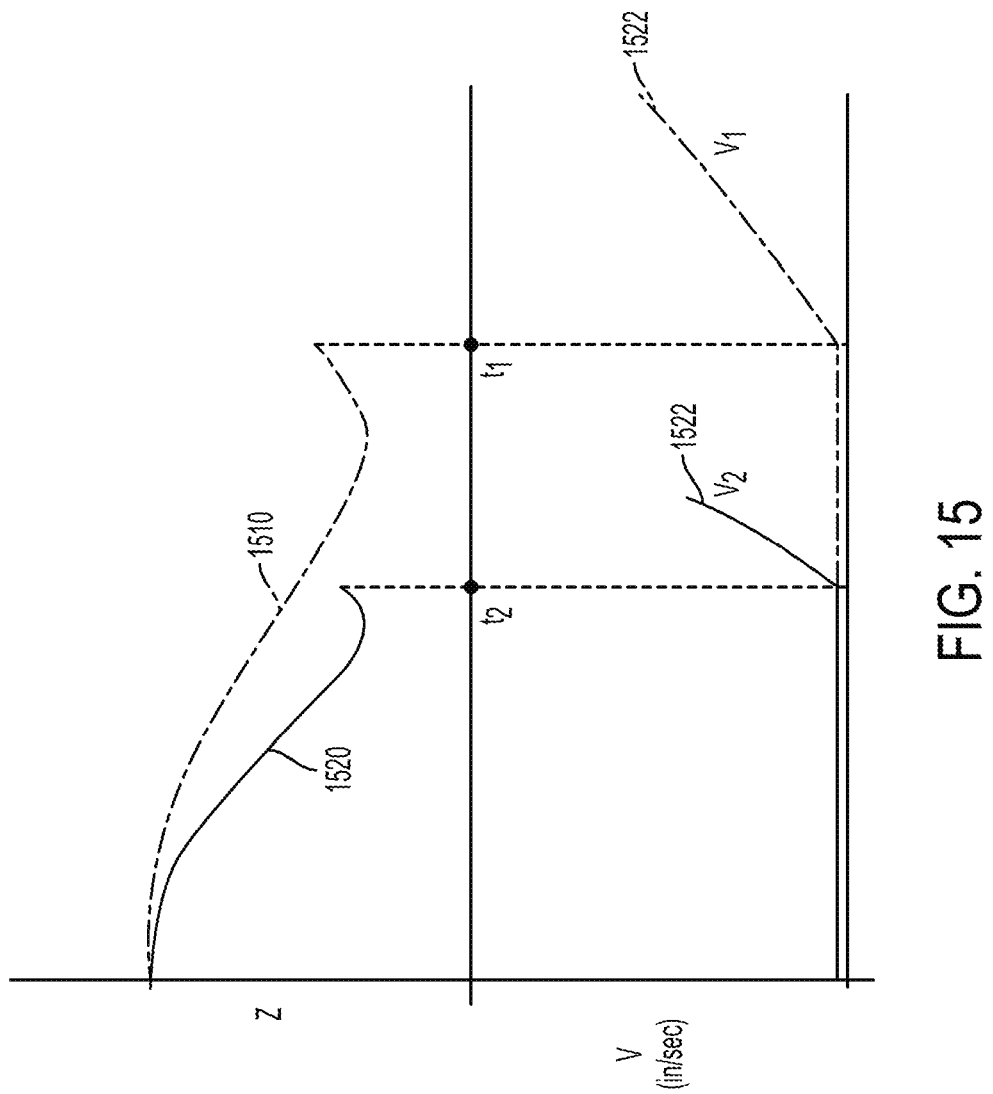
FIG. 15 illustrates impedance curves and lift velocities for different types of tissues.

FIG. 15 illustrates two examples of graphs of trajectory curves representing impedance values and corresponding curves representing lift velocities of end effector's blades for different types of tissues. The impedance curves represent tissue impedance values measured when the end effector, such as the end effector 1400 in FIGS. 14A and 14B, is used to apply ultrasonic energy to tissue when the end effector is in contact with the tissue. The lift velocity curves (which can be, in some cases, linear) represent respective velocities with which the end effector can be automatically lifted once cauterization of tissue having certain characteristics is determined to be complete.

FIG. 15 shows an impedance curve 1510 for one type of tissue, such as a larger (thicker) vessel or other type of tissue. FIG. 15 also shows an impedance curve 1520 for another type of tissue, such as a smaller (thinner) vessel or other type of tissue. The curves 1510, 1520 can be constructed using tissue impedance values (z) as a function of time (t). As shown, both curves 1510, 1520 have a shape resembling a bathtub. In particular, regardless of their specific shapes and length, the curves 1510, 1520 follow a period of a decrease of the initial (relatively high) tissue impedance, which can be followed by a plateau, and then by an increase in electrical impedance of the tissue. The curves 1510, 1520 terminate at first and second time points $t_1$, $t_2$ at which certain threshold impedance values are reached. These indicate a completion of the tissue cauterization process upon which the surgical system can cause a lift of the end effector. It should be appreciated that the time points $t_1$, $t_2$ are referred to herein as "first" and "second" for description purposes only, and not to indicate any order.

The tissue cauterization process and a velocity of a lift of the end effector depend on characteristics of the tissue being treated. FIG. 15 demonstrates by way of example that larger impedance values and a longer time period are required to cauterize a larger vessel than a small vessel. In particular, as shown by the curve 1510, the electrical impedance of the large vessel (or thick tissue) "completes" an "impedance bathtub" at a later (first) time $t_1$. The electrical impedance of the small vessel (or thin tissue) "completes" an "impedance bathtub" at a shorter time period, at the (second) time $t_2$, as shown by the curve 1520.

The described robotic surgical system can use the measured values of tissue impedance and characteristics of a graph (curve) constructed based on these values (in some embodiments, the "impedance bathtub") to determine when the tissue cauterization is complete and thus when, and with which velocity, to automatically lift the end effector. For example, if the curve is indicative of a large vessel and/or thick tissue (e.g., curve 1510), the end effector can be lifted at a slower velocity. If the curve is indicative of a small vessel and/or thinner tissue (e.g., curve 1520), the end effector can be lifted at a higher velocity. FIG. 15 shows (a graph 1512) that a slower lift of the end effector, at a first velocity $v_1$, is used to properly cut a large vessel (or thicker tissue) once the first time period $t_1$ is reached. A small vessel (or thinner tissue) can be cut by a relatively quick lift of the end effector, at a second, smaller velocity $v_2$, once the second time period $t_2$ is reached, as shown by a graph 1522 in FIG. 15. It should be appreciated that the velocities $v_1$, $v_2$ are referred to herein as "first" and "second" for description purposes only, and not to indicate any order.

Figure 16:
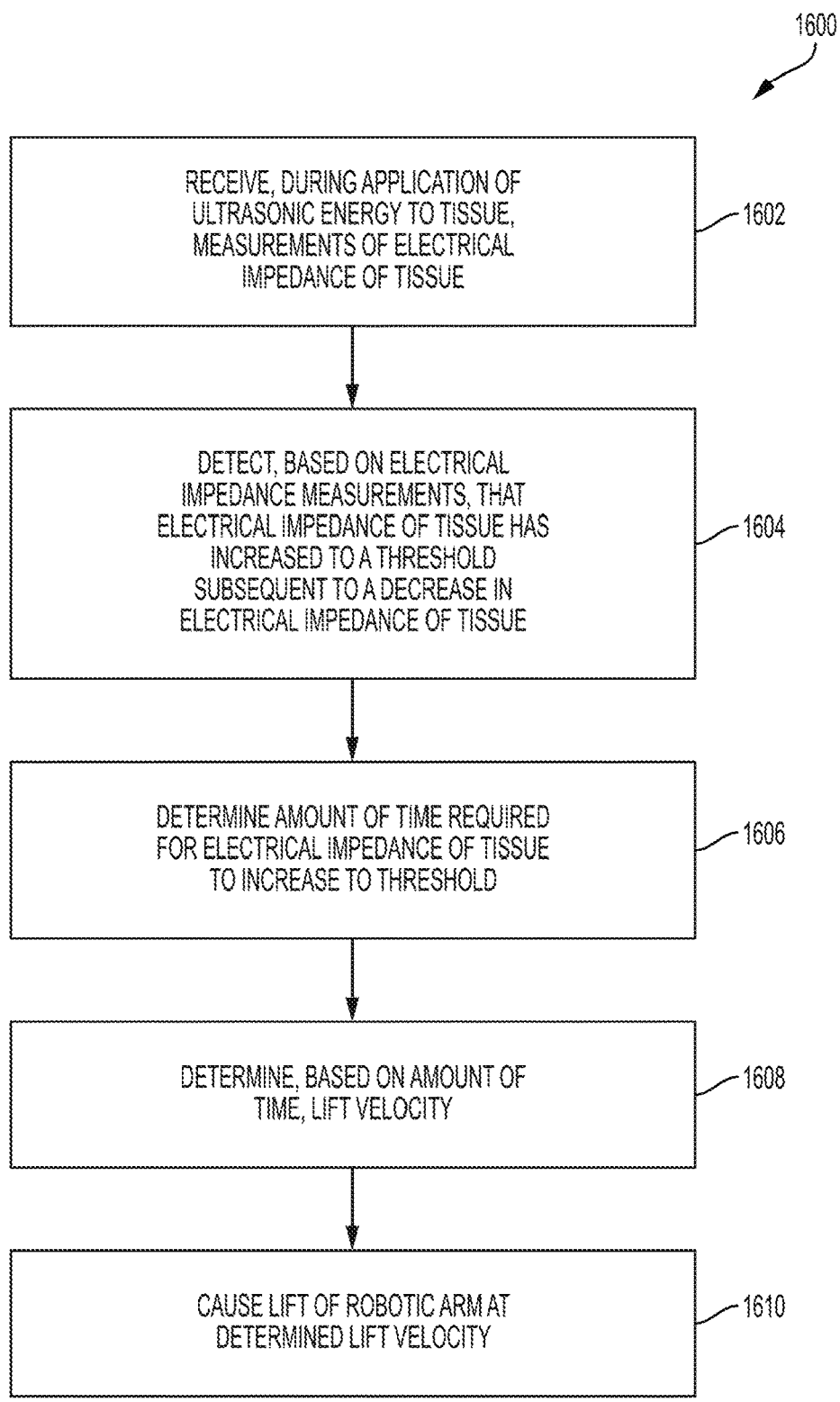
FIG. 16 illustrates an embodiment of a process for cutting and cauterizing tissue.

FIG. 16 is a flowchart illustrating a process 1600 of cutting and cauterizing tissue, in accordance with some embodiments of the current subject matter. The process 1600 can be performed by a robotic surgical system (e.g., the robotic surgical system 300 in FIG. 1) to automate a lift of an electromechanical tool (e.g., tool 330 or 430) having an end effector (e.g., end effector 438 or 1400) adapted to apply ultrasonic energy to tissue coupled thereto. The electromechanical tool can be coupled to a robotic arm (e.g., arm 320 or 420) and can be controlled to be lifted together with the arm, as the arm is being lifted. Additionally or alternatively, the electromechanical tool can be configured to be lifted independently of the robotic arm.

The process 1600 can start when the end effector is activated to hold the tissue and apply ultrasound energy thereto. A person skilled in the art will understand that the process of cutting and cauterizing tissue is performed as part of a surgical procedure that includes other steps (e.g., preparation of the tissue and surgical site, setting and activation of the surgical system, etc.) that are not described herein. The robotic surgical system can receive, during an application of ultrasonic energy to a tissue, a plurality of measurements of electrical impedance of the tissue (1602). For example, the robotic surgical system can receive electrical impedance measurements made at the end effector (e.g., by sensory circuitry such as a bridge circuit) while the end effector is applying ultrasonic energy to tissue, such as a vessel or another type of tissue.

The robotic surgical system can detect, based on the plurality of electrical impedance measurements, that an electrical impedance of the tissue has increased to a threshold subsequent to a decrease in the electrical impedance of the tissue (1604). For example, the robotic surgical system can detect when the electrical impedance of the tissue "completes" an "impedance bathtub." That is, the robotic surgical system can detect when the electrical impedance of the tissue has increased to reach a certain threshold after a period during which the electrical impedance is decreasing. The electrical impedance of the tissue can plateau and/or reach an inflection point prior to the increase. The decrease, plateau, inflection, and subsequent increase of electrical impedance of the tissue can form an impedance curve that resembles a bathtub. These changes in the electrical impedance of the tissue 1430 also correspond to the softening (e.g., denaturing of protein) of the tissue 1430 and the evaporation of fluids (e.g., water) from the tissue 1430 as the tissue 1430 is cauterized by ultrasonic energy from the end effector 1400. Thus, the completion of an impedance bathtub can indicate that the tissue 1430 is fully cauterized. In order to ensure a quality of a seal across the tissue 1430 (e.g., as measured by burst pressure), the tissue 1430 is only cut when the tissue 1430 is fully cauterized (e.g., as indicated by the completion of the impedance bathtub).

In response to detecting that the electrical impedance of the tissue has increased to the threshold, the robotic surgical system can determine an amount of time required for the electrical impedance of the tissue to increase to the threshold (1606). For example, the surgical robotic system 300 can determine an amount of time required for the electrical impedance of the tissue to complete an impedance bathtub. If the tissue is small (or thin), the electrical impedance of the tissue can complete the impedance bathtub in a relatively short period of time (e.g., by the time $t_2$ as shown in the example of FIG. 15). By contrast, if the tissue is large (or thick), the electrical impedance of the tissue can complete the impedance bathtub in a longer period of time (e.g., by the later time $t_1$, as shown in the example of FIG. 15).

The robotic surgical system can determine, based at least in part on the amount of time required for the electrical impedance of the tissue to reach the threshold, a lift velocity (1608). For example, if the electrical impedance of the tissue completes the impedance bathtub in a relatively short amount of time, the tissue is small (or thin) and can be cut with a relatively quick (e.g., high velocity) lift. By contrast, if the electrical impedance of the tissue completes the impedance bath tub in a longer period of time, the tissue is large (or thick) and can be cut with a relatively slow (e.g., low velocity) lift. The lift velocity can also be determined based on a value of the threshold tissue impedance and other parameters that can be controlled and/or monitored during the surgical procedure, such as a clamping pressure applied by the end effector's jaws, and other parameters.

The robotic surgical system can cause a lift of a robotic arm at the determined lift velocity (1610). For example, the surgical robotic system 300 can cause the robotic arm 320 to lift automatically (e.g., heave upward) upon detecting the completion of the impedance bathtub. It should be appreciated that lifting of the robotic arm is shown at 1610 as an example. As mentioned above, in some embodiments, the robotic surgical system can cause a lift of the electromechanical tool, which has the end effector coupled thereto and is mounted on the robotic arm, independently of that arm.

The completion of the impedance bathtub can signal that the tissue is fully cauterized and appropriately sealed. Thus, upon determining (e.g., based on the completion of the impedance bathtub) that the tissue 1430 is fully cauterized, the surgical robotic system 300 can cause an automatic lift of the robotic arm 320. Lifting the robotic arm 320 can cause a corresponding lift of the end effector coupled thereto, which places tension on the tissue (e.g., across the seal). The automatic lift causes the ultrasound blade of the end effector to complete a final cut of the tissue being cut/sealed. The surgical robotic system 300 can cause the robotic arm 320 to lift at a velocity that is appropriate for the size and/or thickness of the tissue. In doing so, the surgical robotic system 300 can ensure a complete cut and seal of the tissue.

It should be appreciated that the process 1600 can include additional and/or different operations than those shown in FIG. 16, without departing from the scope of the present disclosure. Moreover, one or more operations of the process 1600 can be omitted and/or repeated without departing from the scope of the present disclosure.

The techniques described herein can be used in a variety of different surgical contexts involving cutting/sealing of various tissues. Furthermore, although the described robotic surgical system includes a tool such as an end effector configured to apply ultrasonic energy to tissue, the end effector or other surgical instrument can additionally or alternatively be configured to apply radiofrequency (RF) or other type of energy to tissue.

Reuse

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345, entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the described systems and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical system, comprising:
   an electromechanical arm configured for movement in multiple axes;
   an electromechanical tool having an instrument shaft and an end effector formed thereon, the electromechanical tool being configured to be mounted on the electromechanical arm, and the electromechanical tool being configured to move relative to the electromechanical arm and apply ultrasonic energy to tissue held by the end effector;
   a controller operatively coupled to the electromechanical arm and the electromechanical tool, the controller configured to:
   receive, during an application of ultrasonic energy to the tissue, a plurality of measurements of an electrical impedance of the tissue;
   detect, based on the received plurality of measurements, an increase in electrical impedance of the tissue, following a period of decreasing electrical impedance of the tissue; and
   in response to detecting the increase in electrical impedance of the tissue, cause a lift of the electromechanical tool.

2. The surgical system of claim 1, wherein the controller causes the lift of the electromechanical tool independently of the electromechanical arm.

3. The surgical system of claim 1, wherein the controller causes the lift of the electromechanical tool by causing a lift of the electromechanical arm.

4. The surgical system of claim 1, wherein the controller causes the lift of the electromechanical tool at a lift velocity determined at least in part based on the received plurality of measurements.

5. The surgical system of claim 1, wherein detecting the increase in electrical impedance of the tissue by the controller includes detecting that the electrical impedance of the tissue has reached a threshold value.

6. The surgical system of claim 5, wherein the controller is further configured to:
   determine an amount of time required for the electrical impedance of the tissue to reach the threshold value;
   determine, based at least in part on the amount of time, a lift velocity; and
   cause the lift of the electromechanical tool at the determined lift velocity.

7. The surgical system of claim 6, wherein the amount of time required for the electrical impedance of the tissue to reach the threshold value corresponds to at least one characteristic of the tissue.

8. The surgical system of claim 7, wherein the at least one characteristic of the tissue comprises a type, size and/or thickness of the tissue.

9. The surgical system of claim 6, wherein the lift velocity has a first value when the tissue is small and/or thin, and wherein the lift velocity has a second value that is smaller than the first value when the tissue is large and/or thick.

10. The surgical system of claim 1, wherein the end effector includes sensor circuitry adapted to measure the electrical impedance of the tissue while the end effector is applying ultrasonic energy to the tissue.

11. A method of operating a surgical instrument, comprising:
applying ultrasonic energy to a tissue using a surgical instrument formed on an instrument shaft of an electromechanical tool, the electromechanical tool being configured to be mounted on the electromechanical arm;
receiving, during an application of ultrasonic energy to the tissue, a plurality of measurements of an electrical impedance of the tissue;
detecting, based on the received plurality of measurements, an increase in electrical impedance of the tissue, following a period of decreasing electrical impedance of the tissue; and
in response to detecting the increase in electrical impedance of the tissue, causing a lift of the electromechanical tool.

12. The method of claim 11, further comprising causing the lift of the electromechanical tool independently of the electromechanical arm.

13. The method of claim 11, further comprising causing the lift of the electromechanical tool by causing a lift of the electromechanical arm.

14. The method of claim 11, wherein the lift of the electromechanical tool causes the tissue to be cut by placing tension across the tissue.

15. The method of claim 11, wherein detecting the increase in electrical impedance of the tissue by the controller includes detecting that the electrical impedance of the tissue has reached a threshold value.

16. The method of claim 15, further comprising determining that the tissue is fully cauterized when it is detected the electrical impedance of the tissue has reached the threshold value.

17. The method of claim 15, further comprising:
determining an amount of time required for the electrical impedance of the tissue to reach the threshold value;
determining, based at least in part on the amount of time, a lift velocity; and
causing the lift of the electromechanical tool at the determined lift velocity.

18. The method of claim 15, wherein the amount of time required for the electrical impedance of the tissue to reach the threshold value corresponds to at least one characteristic of the tissue.

19. The method of claim 18, wherein the at least one characteristic of the tissue comprises a type, size and/or thickness of the tissue.

20. The method of claim 11, further comprising detecting, based at least in part on the plurality of electrical impedance measurements, following the period of decreasing electrical impedance of the tissue and prior to detecting the increase in electrical impedance of the tissue, that the electrical impedance of the tissue has plateaued and/or reached an inflection point.

21. A method of operating a surgical instrument, comprising:
applying ultrasonic energy to a tissue using a surgical instrument formed on an instrument shaft of an electromechanical tool, the electromechanical tool being configured to be mounted on the electromechanical arm;
receiving, during an application of ultrasonic energy to the tissue, a plurality of measurements of an electrical impedance of the tissue;
detecting, based on the received plurality of measurements, a target trajectory of the electrical impedance of the tissue; and
in response to detecting the target trajectory, causing a lift of the electromechanical tool.

* * * * *